United States Patent [19]

Tracy et al.

[11] 4,294,848
[45] Oct. 13, 1981

[54] THIOCYANO-CONTAINING POLYOXYALKYLENES

[75] Inventors: David J. Tracy, Lincoln Park; Lindley S. Wood, Montclair; Paritosh M. Chakrabarti, Wayne, all of N.J.

[73] Assignee: GAF Corporation, New York, N.Y.

[21] Appl. No.: 174,291

[22] Filed: Jul. 31, 1980

[51] Int. Cl.³ .................. A01N 47/48; C07C 161/02
[52] U.S. Cl. .................................. 424/302; 260/454
[58] Field of Search .................. 260/454; 424/302

[56] References Cited

U.S. PATENT DOCUMENTS

| | | | |
|---|---|---|---|
| 2,372,809 | 4/1945 | Bruson | 260/454 |
| 3,198,821 | 8/1965 | Brotherton et al. | 260/454 |
| 3,252,855 | 5/1966 | Wehner | 424/302 |

Primary Examiner—Dolph H. Torrence

Attorney, Agent, or Firm—James Magee, Jr.; Marilyn J. Maue

[57] ABSTRACT

The thiocyano-containing polyoxyalkylenes having the formula:

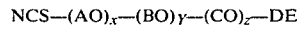

NCS—(AO)$_x$—(BO)$_y$—(CO)$_z$—DE    I.

wherein E is —SCN or a halogen atom; A, C and D represent lower alkylene of 2 to 4 carbon atoms; B is alkylene of 2 to 8 carbon atoms; y and z are each integers having a value of 0 to 50 and x is an integer having a value of from 2 to 50, and intermixtures of said polyoxyalkylenes.

The above compounds display a wide variety of uses, namely for the control of fungi and bacteria or for the prevention of such infestations and infections. They are also useful nematocides and insecticides.

11 Claims, No Drawings

THIOCYANO-CONTAINING POLYOXYALKYLENES

The products of the present invention are particularly effective for control of nematodes such as rootknot, golden nematode, heterodera, schachtii, *D. dipsaci, T. alli, A. secalis*, etc. They are also useful as fungicides for paints and varnishes and as disinfectant cleaners for commercial, e.g. hospital, use.

It is an object of this invention to provide an economical thiocyano-containing polyoxyalkylenes having a wide variety of uses.

Another object of the invention is to provide economical and efficient fungicide.

Another object is to provide a novel group of nematocides and bactericides for commercial use.

These and other objects and advantages of the present invention will become apparent from the following description and disclosure.

According to this invention, there is provided new and useful thiocyano-containing polyoxyalkylenes having the formula:

$$NCS-(AO)_x-(BO)_y-(CO)_z-DE \qquad I.$$

wherein E is —SCN or a halogen atom such as an iodine, chlorine or bromine atom; A, C and D represent lower alkylene of 2 to 4 carbon atoms; B is alkylene of 2 to 8 carbon atoms; y and z are each integers having a value of 0 to 50 and x is an integer having a value from 2 to 50, and intermixtures of said polyoxyalkylenes. Of these compounds, those wherein x, y and z, are taken together average 7 to 60 and A, C and D are the same and are ethylene or isopropylene, are preferred. Of this preferred group, those most desirable are the compounds wherein y and z are 0; x is an integer between 7 and 25 and E is —SCN. However, it is to be understood that the value of x, y and z, as well as the radicals A, B, C and D in the above compounds and their mixtures, can be varied considerably in accordance with the needs of the particular application in which the products are to be employed.

Examples of thiocyano-containing polyoxyalkylenes within the preferred group of compounds include the compounds having the subgeneric formulae:

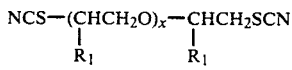

$$NCS-(CHCH_2O)_x-CHCH_2SCN \qquad II.$$
$$\quad\quad\quad\; |\quad\quad\quad\quad\quad\quad |$$
$$\quad\quad\quad R_1\quad\quad\quad\quad\quad R_1$$

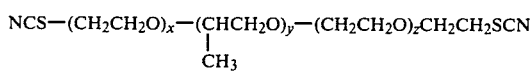

$$NCS-(CH_2CH_2O)_x-(CHCH_2O)_y-(CH_2CH_2O)_zCH_2CH_2SCN \qquad III.$$
$$\quad\quad\quad\quad\quad\quad\quad\quad\quad\quad |$$
$$\quad\quad\quad\quad\quad\quad\quad\quad\quad\; CH_3$$

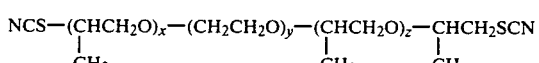

$$NCS-(CHCH_2O)_x-(CH_2CH_2O)_y-(CHCH_2O)_z-CHCH_2SCN \qquad IV.$$
$$\quad\quad\;\;\; |\quad\quad\quad\quad\quad\quad\quad\quad\quad |\quad\quad\quad\quad |$$
$$\quad\quad CH_3\quad\quad\quad\quad\quad\quad\quad\; CH_3\quad\quad\;\; CH_3$$

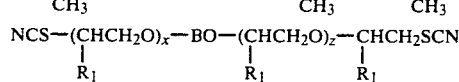

$$NCS-(CHCH_2O)_x-BO-(CHCH_2O)_z-CHCH_2SCN \qquad V.$$
$$\quad\quad\quad\; |\quad\quad\quad\quad\quad\quad\quad\quad |\quad\quad\quad\quad |$$
$$\quad\quad\quad R_1\quad\quad\quad\quad\quad\quad\; R_1\quad\quad\quad R_1$$

wherein, in each of formulae II and V, $R_1$ is hydrogen or methyl and wherein B, in formula V is alkyl of 4 to 8 carbon atoms; x in formula II is an integer having a value of 2 to 25; x and z in formulae III, IV and V are integers having a value of 2 to 20 and y in formulae III and IV is an integer having a value of 1 to 20. It is to be understood that, alternatively, the $C_3$ alkyleneoxy units above may have the structure:

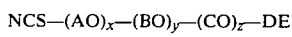

$$-CH_2CHO-$$
$$\quad\quad\; |$$
$$\quad\quad CH_3$$

and these units may comprise the polymeric structure or may be distributed therein in combination with the $C_3$ alkyleneoxy units shown above.

Although it is to be understood that individual compounds within the scope of formula I can be isolated by preparative liquid chromatography or any other standard and convenient method, the products of the present invention are usually employed as mixtures wherein at least x, or x and y, have different values within the above ranges. Such mixtures are also contemplated wherein A, B and/or C represent different alkylene groups, as well. These mixtures have significantly higher boiling points and are more compatible with hydrocarbon chemicals than the individual polymers.

In general, the compounds of the present invention are economical to prepare since most are derived from readily available starting materials. The preparation of the present compounds involves the reaction of a thiocyanide with the dihalide derivative of a polyoxyalkylene glycol having the structure:

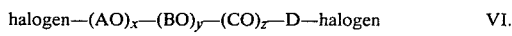

$$halogen-(AO)_x-(BO)_y-(CO)_z-D-halogen \qquad VI.$$

wherein A, B, C and D, as well as x, y and z are as defined above in formula I. The thiocyanide which reacts with the above dihalide is an alkali metal-, calcium- or ammonium-thiocyanide, a tetra-alkyl ammonium thiocyanide of 1 to 18 carbon atoms or thiocyanogen.

The preferred ratio of polyoxyalkylene dihalide to thiocyanide reactant is as close to 1:1 stoichiometry as is convenient to maintain, depending on the product desired. Generally, when a monochloride product is desired as the product of the process, a mole ratio of between about 1.5:1 and about 1:1.5 is satisfactory. However, when it is desirable to replace both terminal halogen atoms with the thiocyano radical, a mole ratio of between about 1:2 and about 1:5 can be employed. It should be understood that, although a higher excess of thiocyano reactant can be employed if desired, there is no benefit to be derived therefrom.

The present reaction is carried out under anhydrous conditions in the presence or in the absence of an inert organic solvent. Suitable solvents, when employed, are those inert organic solvents having a boiling point above the reaction temperature. Typical solvents of this type include toluene, xylene, naphthalene, pyridine, pyrrolidone, cyclohexanol, octanol, chlorobenzene, cycloheptane, dimethylformamide, N-methylpyrrolidone, dimethylsulfoxide, hexamethylphosphoramide and alkanes having from 9 to 12 carbon atoms including cyclic and branched chain hydrocarbons. When employed, the concentration of solvent in the system may vary between about 5 and about 50 weight %, preferably not more than 30 weight %, based on the reactants in the reaction zone.

The present reaction is effected at a temperature of between about 90° C. and about 200° C., under from about 10 to about 50 psi, and is completed in the period of from about 4 to about 20 hours; preferably the reaction is carried out between about 115° C. and about 175° C., under from atmospheric to about 20 psi pressure, and is completed within 8 to about 15 hours, depending upon the degree of conversion desired and the molecular weight of the polymeric reactant. The degree of conversion can be readily determined by measuring the amount of inorganic halide by Volhard titration. Although the reaction can be carried out in an open or a closed system, closed system operation provides better temperature control and means for a more accurate determination of the percent conversion. The non-halogenated products of the present process can be directly obtained in a purity of up to 98%, when a solvent is omitted. However, the solvents, when used, can be easily removed by distillation or any other convenient method.

The polyoxyalkylene dihalides and their intermixtures in the present invention are readily obtained by reacting the corresponding polyalkylene glycols with a molar excess, preferably a 10% to 30% by weight excess, of thionyl halide at moderate temperatures, e.g. between about 50° C. and about 150° C. under atmospheric pressure for a period of from about 6 to about 10 hours. The reaction is described in more detail in Belgian Pat. No. 554,506 filed Jan. 25, 1957 and a general discussion of the glycols is presented in Kirk-Othmer's Encyclopedia of Chemical Technology, second edition, volume 10, page 659.

The polymeric glycols of oxyethylene/oxypropylene are commercially available; e.g. the PLURONIC ® Polyols supplied by Wyandotte Chemicals Corp. of which the Polyols P104, F108, L43, 25R2, 10R5, P85 and F127 are among those most suitable for the polymeric moiety of the polymeric dihalides. Other suitable types are shown in Table I.

TABLE I

| Form | Pluronic Grade | Average Molecular Weight | Flash Point (COC) °F. | Refractive Index 25° C. |
|---|---|---|---|---|
| L | 10R5 | 1970 | >450 | 1.4587 |
| F | 10R8 | 5000 | >450 | — |
| L | 17R1 | 1950 | >450 | 1.4516 |
| L | 17R2 | 2100 | >450 | 1.4535 |
| L | 17R4 | 2700 | >450 | 1.4572 |
| F | 17R8 | 7500 | >450 | — |
| L | 25R1 | 2800 | >450 | 1.4521 |
| L | 25R4 | 3800 | >450 | 1.4574 |
| P | 25R5 | 4500 | >450 | — |
| F | 25R8 | 9000 | >450 | — |
| L | 31R1 | 3200 | >450 | 1.4522 |
| L | 31R2 | 3400 | >450 | 1.4542 |
| P | 31R4 | 4300 | — | — |
|  | L31 | 1100 | 37 | — |
|  | L35 | 1900 | 77 | — |
|  | F38 | 5000 | >100 | 45 |
|  | L42 | 1630 | 37 | — |
|  | L43 | 1850 | 42 | — |
|  | L44 | 2200 | 65 | — |
|  | L61 | 2000 | 24 | — |
|  | L62 | 2500 | 32 | — |
|  | L62LF | 2450 | 28 | — |
|  | L62D | 2750 | 35 | — |
|  | L63 | 2650 | 34 | — |
|  | L64 | 2900 | 58 | — |
|  | P65 | 3500 | 82 | 29.5 |
|  | F68 | 8350 | >100 | 50 |
|  | F68LF | 7700 | 32 | 47 |
|  | F72 | 2850 | 25 | — |
|  | P75 | 4150 | 82 | 34 |
|  | F77 | 6500 | >100 | 48 |
|  | L81 | 2750 | 20 | — |
|  | P84 | 4200 | 74 | 34 |
|  | P85 | 4600 | 85 | 40 |
|  | P87 | 7850 | >100 | 49 |
|  | F88 | 10,800 | >100 | 55 |
|  | F92 | 3500 | 26 | — |
|  | F94 | 4600 | 76 | 38 |
|  | F98 | 13,500 | >100 | 56 |
|  | L101 | 3800 | 15 | — |

TABLE I-continued

| Form | Pluronic Grade | Average Molecular Weight | Flash Point (COC) °F. | Refractive Index 25° C. |
|---|---|---|---|---|
|  | P103 | 4900 | 86 | 30 |
|  | P104 | 5800 | 81 | 37.5 |
|  | P105 | 6350 | 91 | 42 |
|  | F108 | 15,500 | >100 | 57 |
|  | L121 | 4500 | 14 | — |
|  | L122 | 4900 | 19 | — |
|  | F123 | 5650 | 90 | — |
|  | P127 | 11,500 | >100 | 56 |

L - Liquid
P - Paste
F - Flakeable Solid
> - greater than

Many processes are known for the preparation of the glycols, e.g. see volume 10, pages 654-659 of Kirt-Othmer's Encyclopedia of Chemical Technology, second edition. Also, as one of many alternatives, dehydration of

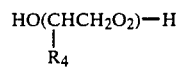

and the oxyalkylene glycol corresponding to —(-BO)$_y$—, e.g.

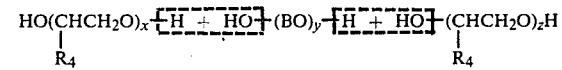

wherein $R_4$ is hydrogen or methyl and B is alkyl of 2 to 8 carbon atoms provides a suitable glycol. A more conventional procedure involves the polymerization of propylene oxide monomer with polyoxyethylene, or vice versa, under basic conditions to provide the mixed glycol polymer. The glycol is then converted to the corresponding halide as described above or by any other known process for preparing the polyoxyalkylene dihalide reactants of this invention.

As stated above, the thiocyano-containing polymeric products of the present invention are useful as additives to formulations, such as paint vehicles, commercial cleansers, oil based lubricants, etc. involves utilization of the present compounds in a wide range of concentrations, e.g. from as little as about 0.05% to about 20% by weight, preferably from about 0.1% to about 10% by weight based on the formulation.

For fungicidal or nematocidal use, the present products are employed in concentrations of between about 100 to about 10,000 ppm in a suitable inert carrier or in a formulation containing other agriculturally active ingredients which do not materially affect the activity of the present thiocyano-containing polymeric products.

Having generally described the invention, reference is now had to the accompanying examples which illustrate preferred embodiments but which are not to be construed as limiting to the scope of the invention as set forth above and as defined in the accompanying claims. All amounts and proportions recited in the following examples are by weight, unless otherwise indicated.

EXAMPLE 1

A. Into a glass round bottom flask, equipped with a mechanical stirrer, a heating mantle, a thermometer and a condenser is added 98 grams of sodium thiocyanide and 436 grams of a polyoxyethylene (PEG-400) dichloride mixture, at pH 7-10, using a catalytic amount of caustic soda and a quaternary ammonia compound. The dichloride reactant has the formula:

Cl—(CH₂CH₂O)$_x$—CH₂CH₂Cl wherein the average value of x is 8. The temperature is then raised to initiate reaction at 120°-140° C. and the reaction mixture is maintained with constant stirring at atmospheric pressure for 4 hours after which heat is withdrawn, the reactor is allowed to cool, sodium chloride filtered and the product contacted with charcoal, after which 395 grams of the corresponding dithiocyano polymeric mixture is collected as a light yellow liquid.

Infrared and elemental analysis agreed with the following structure of the product mixture:

NCS(CH₂CH₂O)$_x$CH₂CH₂SCN

The product, wherein the averaged value of x is 8, is obtained in a yield of 94% or 94% conversion of the dichloride mixture to the corresponding dithiocyanide mixture, calculated by argiometric titration.

B. The above example is repeated except that calcium thiocyanide is substituted for sodium thiocyanide and the product obtained in 95% yield and purity is NCS(CH₂CH₂O)$_x$—CH₂CH₂—SCN. When ammonium thiocyanide is substituted for sodium thiocyanide in part A, the same product as obtained therein is recovered in 90% yield and purity.

EXAMPLE 2

The above example is repeated except that only 49 grams of sodium thiocyanide are added to the reactor and the reaction is terminated when argiometric titration indicated half of the available chlorine is liberated. The product removed from the reactor after filtering sodium chloride is a mixture of mono- and dithiocyanopolyoxyethylenes containing less than 25% unconverted dichloride. The product is primarily a mixture of monothiocyanides and dithiocyanides of the polyoxyethylene, having the formulae:

NCS(CH₂CH₂O)$_x$—CH₂CH₂Cl and
NCS(CH₂CH₂O)$_x$—CH₂CH₂SCN from which the monothiocyanide can be separated by gel permatation chromatography and recovered in 40% yield.

Substitution of polyoxypropylenes or other polyoxyethylenes, such as for example those wherein x is 10, 12 or 21, can be substituted in the above examples 1 and 2 to provide the products corresponding to those indicated in these examples.

EXAMPLE 3

A. Into a glass round bottom flask, equipped as in Example 1, is added 130 grams of potassium thiocyanate and 1180 grams of a polyoxyalkylene dichloride mixture having the formula:

Cl(CH₂CH₂O)$_x$—(CHCH₂O)$_y$—(CH₂CH₂O)$_z$—CH₂CH₂Cl
                |
                CH₃ wherein the averaged value of x+z in the mixture is 12 and the averaged value of y in the mixture is 10. The temperature is raised to 125° C. and is maintained with constant stirring for a period of 15 hours, after which, heating is discontinued and the mixture is allowed to cool to room temperature. After cooling for about 2 hours, the reaction mixture is digested in water and then filtered to remove potassium chloride, and 1050 grams of the corresponding heavy viscous, light yellow product mixture having the formula:

NCS(CH₂CH₂O)$_x$—(CHCH₂O)$_y$—(CH₂CH₂O)$_z$—CH₂CH₂SCN
                    |
                    CH₃ is recovered in 70% yield (based on residual organic chloride). The infrared and elemental analysis agreed with the above indicated structure.

B. The same product as produced in part A is obtained when ammonium thiocyanide or tetralkyl ammonium thiocyanide is substituted for potassium thiocyanide.

EXAMPLE 4

The procedure reported in Example 3 above is repeated except that 1680 grams of a polyoxyalkylene dichloride mixture having the formula:

Cl(CHCH₂O)$_x$—(CH₂CH₂O)$_y$—(CHCH₂O)$_z$—CHCH₂Cl
   |                         |               |
 CH₃                      CH₃          CH₃ wherein the average of x+z in the mixture is 20 and wherein the average of y in the mixture is 10, is substituted for the polyoxyalkylene dichloride employed in Example 3. Similarly, 1650 grams of the corresponding dithiocyano polymeric product mixture, having the formula:

NCS(CHCH₂O)$_x$—(CH₂CH₂O)$_y$—(CHCH₂O)$_z$—CHCH₂SCN
    |                       |               |
  CH₃                     CH₃          CH₃ wherein x, y and z are as defined above in this example is recovered in 50% yield, based on residual organic chloride. Infrared and elemental analysis agreed with the above indicated structure.

EXAMPLE 5

Example 3 is repeated except that 1200 grams of a polyoxyalkylene dichloride mixture having the formula:

Cl(CH₂CH₂O)$_x$—CH₂CH₂CH₂CH₂O—(CH₂CH₂O)$_z$—CH₂CH₂Cl wherein the average of x+z in the mixture is 24, is substituted for the polyoxyalkylene dichloride mixture of Example 3. Similarly, 1150 grams of a corresponding dithiocyano polymeric mixture having the formula:

NCS(CH₂CH₂O)$_x$—CH₂CH₂CH₂CH₂O—(CH₂CH₂O)$_z$—CH₂CH₂SCN where x and z are as defined above in this example, is recovered as a viscous, light yellow liquid.

It is to be understood that other thiocyanocontaining products made from other polymeric mixtures wherein the average of x, y and z is, for example 5, 10, 12, 16, 24 or higher and wherein the polymeric product contains at least two different monomeric units, such as for example wherein A, C and D are ethylene and B is isopropylene or wherein A, C and D are isopropylene and B is ethylene or wherein A, C and D are ethylene or isopropylene and B is butylene, pentylene, hexylene, heptylene or octylene, and many other combinations which are apparent from the foregoing description and disclosure, can be substituted in examples 1 and 2 to produce the corresponding thiocyanate polyoxyalkylene product.

EXAMPLE 6

Activity of the Thiocyano Compound as Nematocide

Root knot was selected for testing since this nematode is distributed world-wide on a wide assortment of crops. Although it resides in root tissues as a parasite where it incites formation of galls, it may also survive in the soil for many months as a scavenger. The following treatment with an aqueous solution of the thiocyanide having the formula:

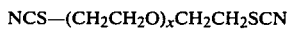

$$NCS-(CH_2CH_2O)_x CH_2CH_2SCN$$

where the average of x is 8, destroys free living forms of root knot and disinfects gall tissue. The procedure is as follows.

Air dry soil and sand were blended in a ratio of 2:1 parts and 6 to 7 grams of chopped galls and root tissues from an infected stock of plants added to each gallon of mixture. Equal portions of the mixture were placed in 4 styrofoam 10 oz. containers to about the ¾ inch level.

To the first container was added 10 ml. of 130 ppm of said thiocyanide in aqueous suspension (equivalent to 12.5 lb/acre). To the second and third containers were added amounts of the standard nematocide, Dasanit, equivalent to 25 lbs/acre and 12.5 lbs/acre respectively. The fourth container of infected soil was left untreated as a control. The containers were then covered with a lid, after 2 hours shaken vigorously, to assure uniform distribution, incubated for 1.5 days and again shaken, after which the covers were removed and soil was leveled. Four cucumber seeds were sown in each container and covered with 30 ml. of sand to a depth of about ¼ inch. The sand in the second and third containers, was sprinkled with a nutrient solution (Miracle Gro at 1 Tsp/gal.) containing a damping-off preventative (Dexon at the rate of 1 Tsp of 35% solution per gal.) to permit growth of vigorous healthy roots.

After 3.5 weeks the roots were washed free of soil, sand and rated according to the severity of infection on a scale of 0 (severe galls) to 10 (no infection). The cucumbers planted in the first container achieved 8 (80%) control of root knot as a result of soil treatment with the thiocyanide of polyoxyethylene. Similar results were achieved with the standard. However, the roots of the cucumbers planted in the infected untreated soil were 100% infected with root knot galls.

EXAMPLE 7

Seven mildew infected rose bushes, five cucumber vines and five peach trees are sprayed to run-off with an aqueous solution containing 500 ppm of the thiocyanide product of Example 1B having the formula:

$$NCS(CH_2CH_2O)_x CH_2CH_2SCN$$

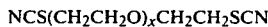

where x is an average of 8. One species of each infected plant is left untreated as a control. After 6 days leaves of each untreated plant are 100% infected with powdery mildew; whereas all treated plants show 0% infection remaining. When the dosage level of the thiocyanide product is reduced to 250 ppm in aqueous solution, only 1% or 2% infection remains.

What we claim is:

1. A thiocyano-containing polyoxyalkylene product having the formula:

$$NCS-(AO)_x-(BO)_y-(CO)_z-DE$$

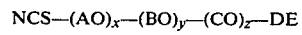

wherein E is halogen or —SCN, A, C and D represent lower alkylene of 2 to 4 carbon atoms; B is alkylene of 2 to 8 carbon atoms; y and z are each integers having a value of from 0 to 50 and x is an integer having a value of from 2 to 50; and intermixtures of said thiocyano-containing polyoxyalkylene compounds.

2. The product of claim 1 wherein said product is a mixture of said thiocyano-containing compounds; x, y and z taken together have an average value of 5 to 60; A and D are the same and are ethylene or isopropylene and E is —SCN.

3. The product of claim 2 wherein y and z are zero and x is an integer having a value between about 7 and 25.

4. The product of claim 3 having the formula:

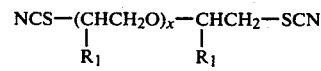

$$NCS-(CHCH_2O)_x-CHCH_2-SCN$$
$$\quad\quad\quad\; |\quad\quad\quad\quad\; |$$
$$\quad\quad\quad R_1\quad\quad\quad\; R_1$$

wherein $R_1$ is hydrogen or methyl and x has an averaged value of 8, 10, 12 or 21.

5. The product of claim 3 having the formula:

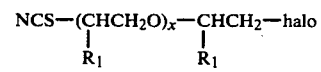

$$NCS-(CHCH_2O)_x-CHCH_2-halo$$
$$\quad\quad\quad\; |\quad\quad\quad\quad\; |$$
$$\quad\quad\quad R_1\quad\quad\quad\; R_1$$

wherein $R_1$ is hydrogen or methyl, halo is a chlorine or bromine atom and x has an averaged value of 8, 10, 12 or 21.

6. The product comprising a mixture of the compounds of claims 4 and 5.

7. The product of claim 1 wherein the product is a mixture of the monothiocyano and dithiocyano polyoxyalkylenes.

8. The product of claim 2 having the formula:

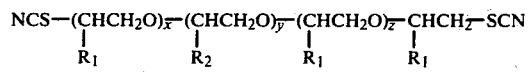

$$NCS-(CHCH_2O)_x-(CHCH_2O)_y-(CHCH_2O)_z-CHCH_2-SCN$$
$$\quad\quad\quad\; |\quad\quad\quad\quad |\quad\quad\quad\quad |\quad\quad\quad\quad\; |$$
$$\quad\quad\quad R_1\quad\quad\quad R_2\quad\quad\quad R_1\quad\quad\quad\; R_1$$

wherein $R_1$ and $R_2$ are each hydrogen or methyl and $R_2$ is other than $R_1$.

9. The product of claim 2 having the formula:

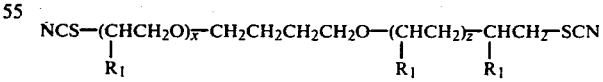

$$NCS-(CHCH_2O)_x-CH_2CH_2CH_2CH_2O-(CHCH_2)_z-CHCH_2-SCN$$
$$\quad\quad\quad |\quad\quad\quad\quad\quad\quad\quad\quad\quad\quad\quad\quad\; |\quad\quad\quad\; |$$
$$\quad\quad\quad R_1\quad\quad\quad\quad\quad\quad\quad\quad\quad\quad\quad\; R_1\quad\quad\; R_1$$

wherein $R_1$ is hydrogen or methyl.

10. The process of contacting a site of infestation of bacteria, fungi or a nematode with between about 0.05 and about 20 weight % of the product of claim 1 to arrest said infestation.

11. An infestation toxin composition comprising between about 2.5 and about 10,000 ppm of the product of claim 1 in an inert carrier therefor to arrest said infestation.

* * * * *